United States Patent [19]

Bender et al.

[11] 3,961,069
[45] June 1, 1976

[54] AKENYL(OR ALKYNYL) 9-XANTHENYL ETHER COMPOUNDS

[75] Inventors: Paul E. Bender, Willingboro, N.J.; Bernard Loev, Broomall, Pa.

[73] Assignee: SmithKline Corporation, Philadelphia, Pa.

[22] Filed: Apr. 23, 1975

[21] Appl. No.: 570,905

[52] U.S. Cl.............................. 424/283; 260/335
[51] Int. Cl.².................................... C07D 311/84
[58] Field of Search..................... 260/335; 424/283

[56] References Cited
UNITED STATES PATENTS 3,558,779   1/1971   Adams et al........................ 424/283

OTHER PUBLICATIONS

Capuano et al., Chem. Ber. (1971) 104(12), pp. 3750–3756.

*Primary Examiner*—Norma S. Milestone
*Attorney, Agent, or Firm*—Joan S. Keps; Richard D. Foggio; William H. Edgerton

[57] ABSTRACT

The compounds are alkenyl(and alkynyl) 9-xanthenyl ethers, for example allyl 9-xanthenyl ether, which are inhibitors of gastric acid secretion.

7 Claims, No Drawings

AKENYL(OR ALKYNYL) 9-XANTHENYL ETHER COMPOUNDS

This invention relates to new alkenyl(and alkynyl) 9-xanthenyl ethers having pharmacological activity. In particular, these compounds inhibit gastric acid secretion.

The compounds of this invention are represented by the following formula:

FORMULA I

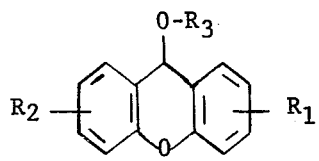

in which:

$R_1$ is hydrogen, halogen, hydroxy, lower alkyl or lower alkoxy;

$R_2$ is hydrogen, halogen, lower alkyl or lower alkoxy;

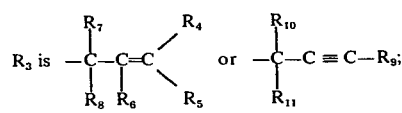

$R_4$, $R_5$, $R_6$ and $R_9$, being the same or different, are hydrogen, methyl or ethyl; and $R_7$, $R_8$, $R_{10}$ and $R_{11}$, being the same or different, are hydrogen or methyl.

Preferably, in compounds of Formula I, $R_1$ and $R_2$, being the same or different, are hydrogen, chloro, methyl or methoxy.

Advantageous compounds of this invention are represented by Formula I in which $R_1$ is hydrogen, chloro, methyl or methoxy, $R_2$ is hydrogen.

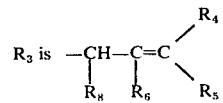

and $R_4$, $R_5$, $R_6$ and $R_8$ are hydrogen or methyl.

Most preferably, in the advantageous compounds of this invention, $R_3$ is —$CH_2CH=CH_2$.

A particularly preferred compound of this invention is allyl 9-xanthenyl ether.

The compounds of this invention produce inhibition of gastric acid secretion. This activity is demonstrated by administration to pylorus ligated rats at doses of about 30 to 50 mg./kg. orally. Also, this activity is demonstrated by intragastric administration to chronic gastric fistula monkeys at doses of about 3.75 to 15 mg./kg. In these procedures, compounds which produce an increase in gastric pH or a decrease in the volume of gastric juice or both are considered active.

These compounds which inhibit gastric acid secretion are useful in treating gastric and duodenal ulcer disease and other conditions involving gastric acid hypersecretion.

The compounds of this invention are prepared by the following procedures:

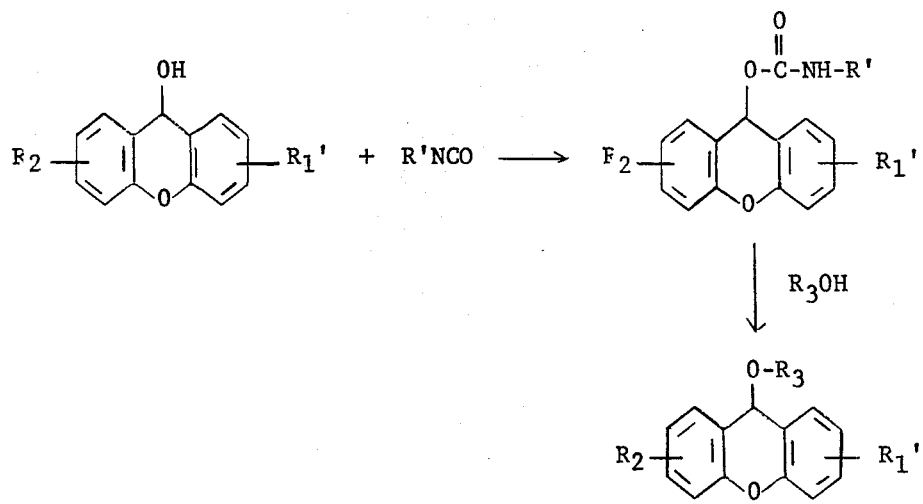

The terms $R_2$ and $R_3$ are as defined above; $R_1'$ is hydrogen, halogen, lower alkyl or lower alkoxy and $R'$ is lower alkyl, preferably methyl.

According to the above procedure I, a xanthydrol is reacted with a lower alkyl isocyanate to give a 9-lower alkylcarbamoyloxyxanthene intermediate. This intermediate is reacted with an alkenyl or alkynyl alcohol of the formula $R_3OH$ to give the alkenyl and alkynyl 9-xanthenyl ether compounds of this invention. The reaction of the 9-lower alkylcarbamoyloxyxanthene with the alcohol is preferably carried out at room temperature. Alternatively, the xanthydrol may be converted to other O-acyl derivatives such as O-alkanoylxanthenes and these intermediates are then reacted with an alcohol ($R_3OH$) to give the ethers of this invention.

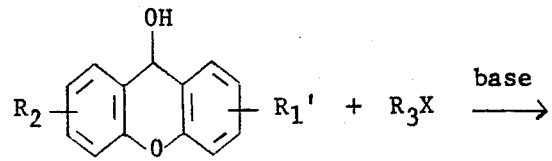

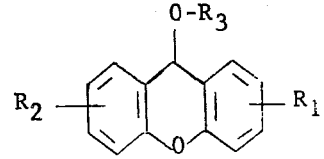

The terms $R_1'$, $R_2$ and $R_3$ are as defined above and X is halogen.

According to procedure II, a xanthydrol compound is reacted with an alkenyl or alkynyl halide in the presence of base such as sodium hydride or butyl lithium to give the alkenyl and alkynyl 9-xanthenyl ether compounds of this invention.

The compounds of Formula I in which $R_1$ is hydroxy are prepared by procedure I by reacting a hydroxy substituted xanthydrol with a lower alkyl isocyanate, then reacting the resulting di(lower alkyl carbamoyloxy)xanthene intermediate with an alkenyl or alkynyl alcohol to give the alkenyl or alkynyl (lower alkylcarbamoyloxy-9-xanthenyl) ether which on treating with base such potassium carbonate in aqueous methanol at elevated temperature gives the ethers of Formula I in which $R_1$ is hydroxy.

The xanthydrol starting materials in procedures I and II above are either known to the art or are prepared by the following procedure:

III.

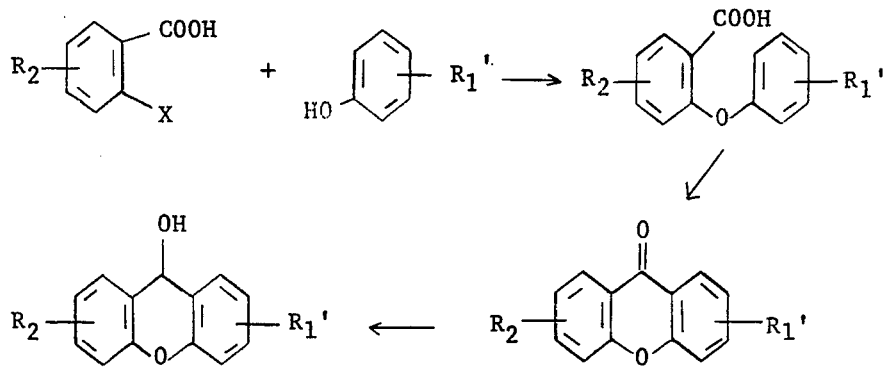

The terms $R_1'$, $R_2$ and $R_3$ are as defined above.

According to the above procedure, a 2-halobenzoic acid is reacted with a phenol preferably in the presence of a base such as potassium carbonate and in the presence of cuprous iodide and copper bronze. The resulting 2-phenoxybenzoic acid is cyclized by treating with acid for example polyphosphoric acid. The resulting xanthone is reduced, for example using sodium amalgam in ethanol, to give the xanthydrol.

The hydroxy substituted xanthydrol starting materials are prepared by treating a methoxy substituted xanthone, prepared by procedure III above, with hydrobromic acid in acetic acid or with pyridine hydrochloride to cleave the methoxy group and reducing the 9-hydroxy group of the resulting hydroxy substituted xanthydrol by the procedure described above.

Preferably, the compounds are administered in conventional dosage forms prepared by combining an appropriate dose of the compound with standard pharmaceutical carriers.

Pharmaceutical compositions having gastric acid secretion inhibitory activity, in dosage unit form, comprising a pharmaceutical carrier and a gastric acid secretion inhibiting amount of a compound of Formula I or a pharmaceutically acceptable acid addition salt thereof are objects of this invention.

The pharmaceutical carrier may be for example a solid or a liquid. Exemplary of solid carriers are lactose, magnesium stearate, terra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The methods of inhibiting gastric acid secretion in accordance with this invention comprise administering internally to an animal an effective amount of a compound of Formula I or a pharmaceutically acceptable acid addition salt thereof. The active ingredients will preferably be administered in dosage unit form as described above.

The compounds of this invention will be administered in a daily dosage regimen of from about 10 mg. to about 2 g., preferably from about 25 mg. to about 1 g. Advantageously, equal doses will be administered one to four times per day. Dosage units will contain from about 10 mg. to about 500 mg., preferably from about 25 mg. to about 300 mg., of the active ingredient.

When administration is carried out as described above, gastric acid secretion is inhibited.

One skilled in the art will recognize that in determining the amounts of the active ingredients in the claimed compositions and used in the claimed methods, the activity of the chemical ingredient as well as the size of the host animal must be considered.

The terms "lower alkyl" and "lower alkoxy" where used herein denote groups having, preferably, 1–4 carbon atoms and "halogen" denotes chloro, bromo or fluoro.

The following examples are not limiting but are illustrative of the invention.

EXAMPLE 1

Methyl isocyanate (20 g.) was added slowly, with stirring, to a filtered solution of 30 g. of xanthydrol in 100 ml. of anhydrous triethylamine. After standing for 40 minutes in 20°C. water bath, the mixture was filtered. The collected solid was washed with anhydrous diethyl ether and dried in vacuo to give 9-(N-methylcarbamoyloxy)xanthene.

9-(N-Methylcarbamoyloxy)xanthene (27.0 g., 0.016 moles) was stirred with 150 ml. of allyl alcohol for 1.5 hours at room temperature, and the mixture was then filtered. The filtrate was evaporated in vacuo, and the residue was dissolved in 200 ml. of ice-cold ether and washed twice each with 100 ml. portions of ice-cold 10% aqueous acetic acid, water and 5% aqueous sodium bicarbonate solution. After drying over potassium carbonate, the solvent was removed in vacuo, and the resulting oil was distilled to give allyl 9-xanthenyl ether, b.p. 100°–105°C. at 0.005 mm.

EXAMPLE 2

9-(N-Methylcarbamoyloxy)xanthene (3.0 g., 11.8 mmoles.) was stirred with 18 ml. of propargyl alcohol for 1.5 hours at room temperature, and the mixture was then filtered. The filtrate was evaporated in vacuo, and the residue was dissolved in ice-cold ether and washed twice with 20 ml. of ice-cold 10% aqueous acetic acid, 15 ml. of ice-cold water, and 10 ml. of ice-cold 5% aqueous sodium bicarbonate solution. After drying over potassium carbonate, the solvent was removed in vacuo. The resulting solid was recrystallized from hexane to give propargyl 9-xanthenyl ether, m.p. 74°–76°C.

EXAMPLE 3

9-(N-Methylcarbamoyloxy)xanthene (6.0 g., 23.5 mmoles) was stirred with 15 ml. of 2-buten-1-ol for 1.5 hours at room temperature, and the mixture was then filtered. The filtrate was evaporated in vacuo, and the residue was dissolved in ice-cold ether and washed twice with ice-cold portions of 10% aqueous acetic acid, water and 5% aqueous sodium bicarbonate solution. After drying over potassium carbonate, the solvent was removed in vacuo, and the resulting oil was distilled to give 2-buten-1-yl 9-xanthenyl ether, b.p. ca. 110°C. at 0.01 mm.

EXAMPLE 4

9-(N-Methylcarbamoyloxy)xanthene (4.0 g., 15.7 mmoles) was stirred with 20 ml. of 2-methyl-2-propen-1-ol for 20 hours at room temperature, and the mixture was then filtered. The filtrate was evaporated in vacuo and the residue was dissolved in ice-cold ether and washed twice with ice-cold portions of 10% aqueous acetic acid, water, and 5% aqueous sodium bicarbonate solution. After drying over potassium carbonate, the solvent was removed in vacuo, and the resulting oil was distilled to give (2-methyl-2-propen-1-yl) 9-xanthenyl ether, b.p. 116°C. at 0.15 mm.

EXAMPLE 5

9-(N-Methylcarbamoyloxy)xanthene (6.0 g., 23.5 mmoles) was stirred with 30 ml. of 3-methyl-2-buten-1-ol for 3 hours at room temperature, and the mixture was then filtered. The filtrate was evaporated in vacuo, and the residue was dissolved in ice-cold ether and washed twice with ice-cold portions of 10% aqueous acetic acid, water, and 5% aqueous sodium bicarbonate solution. After drying over potassium carbonate, the solvent was removed in vacuo, and the resulting oil as distilled to give (3-methyl-2-buten-1-yl) 9-xanthenyl ether, b.p. ca. 110°C. at 0.01 mm.

EXAMPLE 6

By the procedure of Example 1 using, in place of allyl alcohol, the following alcohols:
3-buten-2-ol
2-methyl-3-buten-2-ol
2-penten-1-ol
3-butyn-2-ol
2-methyl-3-butyn-2-ol
2-pentyn-1-ol
the following products are prepared, respectively:
3-buten-2-yl 9-xanthenyl ether
(2-methyl-3-buten -2-yl) 9-xanthenyl ether
2-penten-1-yl 9-xanthenyl ether
3-butyn-2-yl 9-xanthenyl ether
(2-methy-3-butyn-2-yl) 9-xanthenyl ether
2-pentyn-1-yl 9-xanthenyl ether.

EXAMPLE 7

Using 2-chloroxanthydrol in place of xanthydrol in the procedure of Example 1 gives, as the product, allyl 2-chloro-9-xanthenyl ether.

Similarly, using the following substituted xanthydrol compounds in the procedure of Example 1:
3-chloroxanthydrol
1-chloroxanthydrol
4-chloroxanthydrol
3-fluoroxanthydrol
2-bromoxanthydrol
the following products are obtained, respectively:
allyl 3-chloro-9-xanthenyl ether
allyl 1-chloro-9-xanthenyl ether
allyl 4-chloro-9-xanthenyl ether
allyl 2-fluoro-9-xanthenyl ether
allyl 2-bromo-9-xanthenyl ether.

EXAMPLE 8

Reacting 3-methylxanthydrol with methyl isocyanate by the procedure of Example 1 gives 3-methyl-9-(N-methylcarbamoyloxy)xanthene.

By the procedure of Example 2, the above prepared xanthene compound is reacted with propargyl alcohol to give propargyl 3-methyl-9-xanthenyl ether.

EXAMPLE 9

By the procedure of Example 1, using the following in place of xanthydrol:
2-methylxanthydrol
2-ethylxanthydrol
2-t-butylxanthydrol
2-methoxyxanthydrol
3-methoxyxanthydrol
2-ethoxyxanthydrol
the following products are obtained, respectively:
allyl 2-methyl-9-xanthenyl ether
allyl 2-ethyl-9-xanthenyl ether
allyl 2-t-butyl-9-xanthenyl ether allyl 2-methoxy-9-xanthenyl ether
allyl 3-methoxy-9-xanthenyl ether
allyl 2-ethoxy-9-xanthenyl ether.

EXAMPLE 10

Usng 2,7-dibromoxanthydrol in place of xanthydrol in the procedure of Example 1 gives allyl 2,7-dibromo-9-xanthenyl ether.

Similarly using the following substituted xanthydrols in the procedure of Example 1:
 1,7-dimethoxyxanthydrol
 1,8-dimethylxanthydrol
the products are, respectively:
 allyl 1,7-dimethoxy-9-xanthenyl ether
 allyl1,8-dimethyl-9-xanthenyl ether.

EXAMPLE 11

A suspension of 25 g. of 3-chloro-6-methoxyxanthone in 175 ml. of 95% aqueous ethanol is poured into a flask containing sodium amalgam prepared from 9.0 g. of sodium and 55 ml. of mercury. The flask is stoppered and shaken vigorously for 20 minutes with intermittant venting. The amalgam is then allowed to settle and the ethanolic supernatant is decanted into 1.5 liters of water. The precipitate is filtered from the resulting mixture, washed with water, and air dried to yield 3-chloro-6-methoxyxanthydrol.

Using 3-chloro-6-methoxyxanthydrol in place of xanthydrol in the procedure of Example 1 gives allyl 3-chloro-6-methoxy-9-xanthenyl ether.

By the same procedure, using the following xanthones as the starting materials:
 2-propylxanthone
 3,6-dichloroxanthone
 3-methoxy-6-methylxanthone
 6-methoxy-2-methylxanthone
 3-hydroxyxanthone
 2-hydroxyxanthone
 6-hydroxy-2-methylxanthone
the following products are obtained, respectively:
 allyl 2-propyl-9-xanthenyl ether
 allyl 3,6-dichloro-9-xanthenyl ether
 allyl 3-methoxy-6-methyl-9-xanthenyl ether
 allyl 6-methoxy-2-methyl-9-xanthenyl ether
 allyl 3-hydroxyxanthenyl ether
 allyl 2-hydroxyxanthenyl ether
 allyl 6-hydroxy-2-methylxanthenyl ether.

EXAMPLE 12

| Ingredients | Amounts |
|---|---|
| Allyl 9-xanthenyl ether | 200 mg. |
| Lactose | 80 mg. |
| Magnesium stearate | 5 mg. |

The ingredients are mixed and filled into a hard gelatin capsule.

EXAMPLE 13

| Ingredients | Amounts |
|---|---|
| Allyl 9-xanthenyl ether | 150 mg. |
| Calcium sulfate dihydrate | 125 mg. |
| Sucrose | 25 mg. |
| Starch | 15 mg. |
| Talc | 5 mg. |
| Stearic acid | 3 mg. |

The sucrose, calcium sulfate dihydrate and allyl 9-xanthenyl ether are mixed and granulated with 10% gelatin solution. The wet granules are screened, dried and then mixed with the starch, talc and stearic acid, screened and compressed into a tablet.

What is claimed is:

1. A compound of the formula:

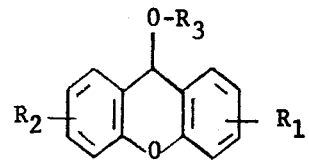

in which:
 $R_1$ is hydrogen, halogen hydroxy, lower alkyl or lower alkoxy;
 $R_2$ is hydrogen, hydroxy, lower alkyl or lower alkoxy;

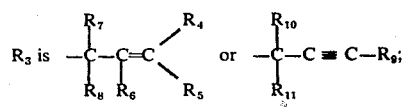

$R_4$, $R_5$, $R_6$ and $R_9$, being the same or different, are hydrogen, methyl or ethyl; and
 $R_7$, $R_8$, $R_{10}$ and $R_{11}$, being the same or different, are hydrogen or methyl.

2. A compound of claim 1 in which $R_1$ and $R_2$, being the same or different, are hydrogen, chloro, methyl or methoxy.

3. A compound of claim 2 in which $R_2$ is hydrogen,

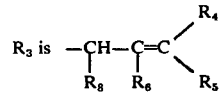

and $R_4$, $R_5$, $R_6$ and $R_8$ are hydrogen or methyl.

4. A compound of claim 3 in which $R_3$ is —CH$_2$CH=CH$_2$.

5. A compound of claim 1 said compound being allyl 9-xanthenyl ether.

6. A pharmaceutical composition having gastric acid secretion inhibitory activity comprising a pharmaceutical carrier and a compound of claim 1.

7. A method of inhibiting gastric acid secretion comprising administering to an animal a compound of claim 1.

* * * * *

UNITED STATES PATENT AND TRADEMARK OFFICE
CERTIFICATE OF CORRECTION

PATENT NO. : 3,961,069
DATED : June 1, 1976
INVENTOR(S) : Paul E. Bender and Bernard Loev It is certified that error appears in the above-identified patent and that said Letters Patent are hereby corrected as shown below:

Column 2, directly below line 21, insert -- I. -- .

Column 2, directly below line 57, insert -- II. -- .

Column 6, at the end of line 7, "as" should read -- was -- .

Column 8, line 27, insert a comma after "halogen" .

Signed and Sealed this

Twenty-first Day of September 1976

[SEAL]

Attest:

RUTH C. MASON
*Attesting Officer*

C. MARSHALL DANN
*Commissioner of Patents and Trademarks*